US008988679B2

(12) United States Patent
Natan (10) Patent No.: US 8,988,679 B2
(45) Date of Patent: Mar. 24, 2015

(54) SERS NANOTAG ASSAYS (75) Inventor: Michael J. Natan, Los Altos, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 719 days.

(21) Appl. No.: 12/596,089

(22) PCT Filed: Apr. 18, 2008

(86) PCT No.: PCT/US2008/060871
§ 371 (c)(1),
(2), (4) Date: Mar. 29, 2010

(87) PCT Pub. No.: WO2009/009198
PCT Pub. Date: Jan. 15, 2009

(65) Prior Publication Data
US 2010/0177306 A1  Jul. 15, 2010

(51) Int. Cl.
G01J 3/44       (2006.01)
G01N 33/566   (2006.01)
G01N 21/65     (2006.01)
B82Y 30/00     (2011.01)
C40B 70/00    (2006.01)
B82Y 20/00     (2011.01)

(52) U.S. Cl.
CPC ........ *C40B 70/00* (2013.01); *B01J 2219/00576* (2013.01); *G01N 21/658* (2013.01); *B82Y 30/00* (2013.01); *B01J 2219/00572* (2013.01); *B01J 2219/00725* (2013.01); *B82Y 20/00* (2013.01); *G01N 2201/06193* (2013.01); *B01J 2219/00722* (2013.01); *Y10S 977/773* (2013.01)
USPC ............................ 356/301; 977/773; 436/501

(58) Field of Classification Search
CPC ... G01N 21/658; G01N 21/65; G01N 21/553; G01N 21/554; G01N 33/54346; G01N 2021/655; G01N 33/587; G01J 3/44
USPC .................................................. 356/301–318
See application file for complete search history.

(56) References Cited

U.S. PATENT DOCUMENTS

| 6,149,868 A | 11/2000 | Natan et al. |
| 6,514,767 B1 | 2/2003 | Natan |
| 6,861,263 B2 | 3/2005 | Natan |
| 7,123,359 B2 * | 10/2006 | Armstrong et al. ........... 356/301 |
| 7,192,778 B2 | 3/2007 | Natan |
| 7,443,489 B2 | 10/2008 | Natan |

(Continued)

Primary Examiner — Tarifur Chowdhury
Assistant Examiner — Sunghee Y Gray
(74) Attorney, Agent, or Firm — Mark Lindsey (57) ABSTRACT A method of producing a surface enhanced Raman scattering spectrum which is useful for certain types of assays, in particular proximity assays. The method includes providing two SERS-active nanoparticles. The first SERS-active nanoparticle will absorb a photon at a first wavelength and emit a Raman-shifted photon at a second wavelength. The second SERS-active nanoparticle will absorb a photon at the second wavelength and emit a Raman-shifted photon at a third wavelength. Accordingly, when the first and second SERS-active nanoparticles are proximate to one another and the first SERS-active nanoparticle is illuminated at the first wavelength a Raman-shifted photon at the second wavelength may be emitted. This photon can be absorbed by the second SERS-active nanoparticle causing detectable emission of a second Raman-shifted photon at the third wavelength. Various assays may be designed based upon the above. Proximity assays using two SERS-active nanoparticles will have advantageous background signal characteristics.

16 Claims, 3 Drawing Sheets

(56) References Cited

U.S. PATENT DOCUMENTS

| | | |
|---|---|---|
| 7,723,100 B2 | 5/2010 | Natan et al. |
| 7,981,695 B2 * | 7/2011 | Schultz et al. ............... 436/525 |
| 8,409,863 B2 | 4/2013 | Natan et al. |
| 8,497,131 B2 | 7/2013 | Natan et al. |
| 2001/0002275 A1 | 5/2001 | Oldenburg et al. |
| 2003/0043366 A1 | 3/2003 | Ohta et al. |
| 2003/0207296 A1 * | 11/2003 | Park et al. ..................... 435/6 |
| 2005/0147976 A1 | 7/2005 | Su |
| 2005/0221494 A1 * | 10/2005 | Natan ............................. 436/56 |
| 2006/0033910 A1 * | 2/2006 | Sun et al. ...................... 356/301 |
| 2006/0038979 A1 | 2/2006 | Natan |
| 2006/0134694 A1 | 6/2006 | Yamakawa |
| 2007/0070341 A1 * | 3/2007 | Wang ............................ 356/301 |
| 2007/0077588 A1 | 4/2007 | Will |
| 2008/0074661 A1 * | 3/2008 | Zhang et al. .................. 356/301 |
| 2009/0155811 A1 | 6/2009 | Natan et al. |
| 2009/0298197 A1 | 12/2009 | Natan et al. |
| 2011/0275061 A1 | 11/2011 | Weidemaier et al. |
| 2012/0164624 A1 | 6/2012 | Natan et al. |
| 2013/0011851 A1 | 1/2013 | Natan et al. |

\* cited by examiner

SERS NANOTAG ASSAYS

TECHNICAL FIELD

The disclosed embodiments are directed toward methods and systems for the use of SERS-active nanoparticles or Surface Enhanced Raman Scattering nanotags (SERS nanotags) to create or implement a variety of assay platforms.

BACKGROUND

Countless types of biological assay, chemical assay, immunoassay or similar assays and tests are known in the biological, chemical, forensic, genomic, medical and genetic arts. Many of these assays or tests feature the detection of a substance or analyte which has been marked or otherwise associated with a tag which makes detection easier, faster, more reliable or otherwise improved.

Known tags may be limited in many ways. For example the tag may be difficult to associate with an analyte or it may be difficult to detect, in particular known tags may be difficult to detect rapidly, accurately or in very small quantities. Known tags may be subject to degradation. Known tags may alter the properties of or otherwise interact with the material or analyte being detected. In addition known tags and families of tags may not include enough members to allow for highly multiplexed tests where numerous independent types of tags are distinctly read or sorted.

The present invention is directed toward overcoming one or more of the problems discussed above.

SUMMARY OF THE EMBODIMENTS

Several methods and systems are disclosed for the use of Surface Enhanced Raman Scattering nanotags (SERS nanotags) to create or enhance assay platforms. The assay formats specifically described herein are not intended to be limiting upon the scope of this invention. Thus, any assay, test, diagnostic protocol or similar technique which features the use of a separate tag element may be implemented with SERS nanotags. Assays featuring SERS nanotags may be used to detect any analyte of interest including but not limited to the detection of cells, viruses, bacteria, proteins, DNA, RNA, or small molecules in any type of biological (animal or plant kingdom) or environmental samples including but not limited to whole blood or serum, occult samples, urine, feces, air, drinking water, phage, any organism, multicellular clumps of cells, for example, cancer tissue homogenate, inorganic compounds or any other type of analyte.

One embodiment is a method of producing a surface enhanced Raman scattering spectrum which is useful for certain types of assays, in particular proximity assays. The method includes providing two SERS-active nanoparticles. The first SERS-active nanoparticle will absorb a photon at a first wavelength and emit a Raman-shifted photon at a second wavelength. The second SERS-active nanoparticle will absorb a photon at the second wavelength and emit a Raman-shifted photon at a third wavelength. Accordingly, when the first and second SERS-active nanoparticles are proximate to one another and the first SERS-active nanoparticle is illuminated at the first wavelength a Raman-shifted photon at the second wavelength may be emitted. This photon can be absorbed by the second SERS-active nanoparticle causing detectable emission of a second Raman-shifted photon at the third wavelength. Various assays may be designed based upon the above. Proximity assays using two SERS-active nanoparticles will have advantageous background signal characteristics.

Various techniques may be utilized to prepare first and second SERS-active nanoparticles which have different absorption and emission characteristics. The first and second nanoparticles may have different shapes. The first nanoparticle may be spherical and the second nanoparticle non-spherical. Alternatively, the first nanoparticle may be solid and the second nanoparticle hollow. The composition of the respective SERS-active nanoparticles may also effect their absorption and emission characteristics. For example, the first SERS-active nanoparticle may be of uniform composition and the second SERS-active nanoparticle having different compositions in separate structures such as a core and shell. Different emission characteristics may also be caused by different materials used to fabricate the respective SERS-active nanoparticles. For example, one nanoparticle may be fabricated from a single metal such as Au and the second particle an alloy or mixture of Au with another substance. Alternatively, particles of different metallic elements, mixtures or alloys thereof, may be utilized.

As described above, the absorbance and emission characteristics of the first and second nanoparticles will be different. For example, an absorbance maximum of the first SERS-active nanoparticle may be separated from an absorbance maximum of the second SERS-active nanoparticle by between 200 $cm^{-1}$ and 3500 $cm^{-1}$. Alternative suitable separations between absorbance or emission characteristics may fall within or outside of this range.

The relationship between the first and second emission wavelength or frequencies may, in certain instances, be directly related to the illumination wavelength or frequency. For example, a SERS reporter may be used which possesses a SERS-active vibrational peak at energy v1. Detection of the Raman-shifted photon emitted at the third wavelength may be accomplished at a frequency of L-(2v1) where L is the first wavelength which corresponds to the laser excitation frequency.

The methods described above may be used to implement various types of proximity assay where at least two SERS-active nanoparticles are brought into close proximity with one another. The first nanoparticle is excited at a first wavelength and emits at a second wavelength. The second SERS-active nanoparticle may then be excited at the second wavelength and emit at a third wavelength. The assay will include a detector configured to detect light at the third wavelength. A proximity assay as described above features relative immunity from background emissions. The proximity assay may be implemented with any type of SERS-active nanoparticle as described above.

DETAILED DESCRIPTION OF THE INVENTION

I. General Discussion of SERS Nanotags and SERS Active Nanoparticles

Many of the assays described herein feature SERS-active nanoparticles or SERS nanotags. As used herein a SERS-active nanoparticle is a nano-sized particle which has a surface suitable for Raman scattering enhancement. For example, a gold or silver nanoparticle. Other materials may be used to fabricate a SERS-active nanoparticle as well. As described below, the SERS-active nanoparticles may have various shapes and structures. The key feature of a SERS-active nanoparticle is that it has a surface which will enhance a Raman spectrum. A SERS-active nanoparticle may be associated with a Raman-active substance such as a Raman reporter or Raman dye. Alternatively, the SERS-active nanoparticle may not be associated with a Raman active substance. A SERS-active nanoparticle may be functionalized with or encapsulated by any number of substances. For example, one specific type of nanoparticle, a SERS-nanotag as described in detail below, is typically encapsulated. Thus, the nanoparticle core of a SERS nanotag is itself a SERS-active nanoparticle.

SERS nanotags offer at least six intrinsic advantages as detection tags. (1) While they can be excited over a wide range of wavelengths, in particular SERS tags can be excited in the near-IR, and thus are compatible with measurements in whole blood. (2) SERS nanotags resist photobleaching which allows for higher laser powers and longer data acquisition times, resulting in more sensitive measurements. (3) A large number of distinct tags exist, enabling highly multiplexed assays. (4) SERS nanotags are non-reactive with many analytes and substrates (5) SERS nanotags are durable. (6) SERS nanotags are easily handled and stored. Thus, SERS tags are aggregation resistant, stabilized against decomposition in solvent and air, chemically inert, and can be centrifuged and redispersed without loss of SERS activity.

In some embodiments, SERS nanotags are used in biological and chemical assays as replacements for fluorescent tags. Indeed, SERS nanotags possess a number of characteristics that make them far superior to prior art optical tags based on fluorophores. For example, assays using fluorophore detection are commonly hampered by the presence of autofluorescence and other background effects. In addition, many assays require use of a number of different fluorophores; different fluorophores commonly require different attachment chemistries and have different environmental requirements and sensitivities. Particularly noteworthy is the quenching of fluorescent activity that is observed when some fluorophores are conjugated to proteins. Finally, irreversible photodegradation resulting from the creation of a triplet or singlet excited state, followed by a non-reversible chemical reaction that permanently eliminates the excited state—places a severe limitation on the sensitivity of detection. By contrast, SERS nanotags cannot be photobleached or photodegraded, they have uniform chemical and physical properties, and they can be readily resolved from the background.

SERS nanotags are novel, nanoparticulate optical detection tags based on surface enhanced Raman scattering (SERS) (Mulvaney et al. (2003) *Langmuir* 19:4784-4790; Natan, U.S. Pat. No. 6,514,767). Raman scattering (Long (2002) *The Raman Effect; A Unified Treatment of the Theory of Raman Scattering by Molecules*. John Wiley & Sons Ltd, Chichester; *Modern Techniques in Raman Spectroscopy* (1996) John Wiley & Sons Ltd, Chichester; *Analytical Applications of Raman Spectroscopy* (1999) Blackwell Science Ltd, Malden, Mass.) SERS is a laser-based optical spectroscopy that, for molecules, generates a fingerprint-like vibrational spectrum with features that are much narrower than typical fluorescence. Raman scattering can be excited using a broad range of wavelengths including monochromatic far-red or near-IR light, photon energies which are too low to excite the inherent background fluorescence in biological samples. Since Raman spectra typically cover vibrational energies from 300-3500 $cm^{-1}$, it could be possible to measure a dozen (or more) tags simultaneously, all with a single light source. However, normal Raman spectra are very weak, limiting utility for bioanalytical chemistry. In SERS, molecules in very close proximity to nanoscale roughness features on noble metal surfaces (gold, silver copper) give rise to million- to trillion-fold increases [known as enhancement factor (EF)] in scattering efficiency (Moskovits (1985) *Rev. Mod. Phys.* 57:783-826; Otto et al. (1992) *J. Phys. Cond. Mat.* 4:1143-1212; Campion and Kambhampati (1998) *Chem. Soc. Rev.* 27:241-249; Tian et al. (2002) *J. Phys. Chem. B* 106:9463-9483; CAS Online Search, April 2004), Surface-Enhanced Raman Scattering:Physics and Applications, Kneipp, K., Moskovits, M., and Kneipp, H., Ed. Springer-Verlag, 2007, Berlin Heidelberg.

More importantly, SERS can also be used to detect molecules adsorbed to individual metal nanoparticles (Emory et al. (1998) *J. Am. Chem. Soc.* 120:8009-8010; Moyer et al. (2000) *J. Am. Chem. Soc.* 122:5409-5410), and has been used to demonstrate detection of single molecules (Nie and Emory (1997) *Science* 275:1102-1106; Kneipp et al. (1997) *Phys. Rev. Lett.* 78:1667-1670; Michaels et al. (1999) *J. Am. Chem. Soc.* 121:9932-9939; Xu et al. (1999) *Phys. Rev. Lett.* 83:4357-4360; Goulet et al. (2003) *Anal. Chem.* 75:1918-1923).

Figure 1:
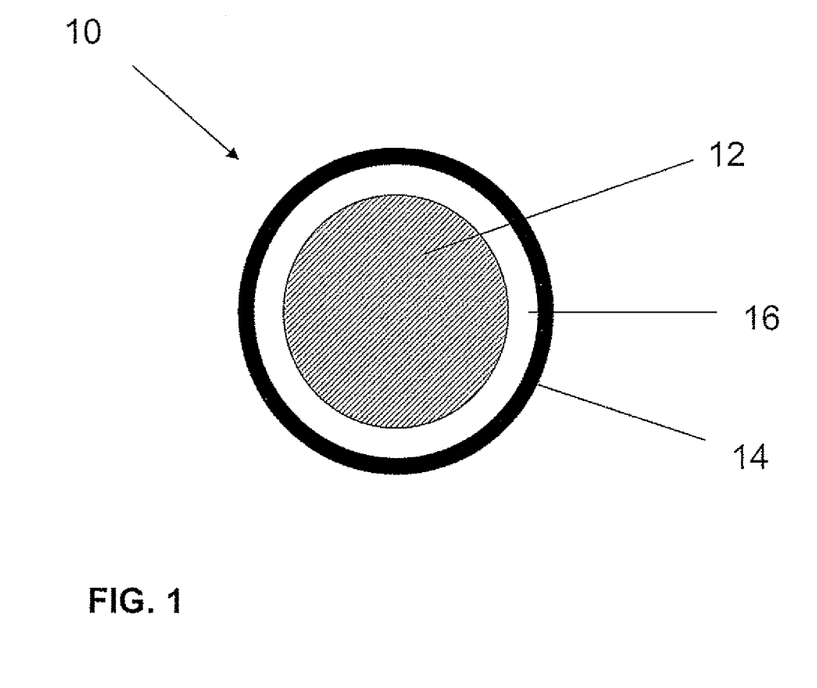
FIG. 1 is a schematic diagram of a SERS nanotag suitable for implementation of select embodiments of the present invention.

A typical SERS nanotag 10 is shown in FIG. 1. The illustrated SERS nanotag 10 includes a metal nanoparticle core 12, and a $SiO_2$ (silica) shell 14. Other materials including but not limited to various types of polymers may also be used as an encapsulant or shell in a manner consistent with the present invention. In addition, polymers can be used as reporters, and multifunctional polymers could be used both as reporter and encapsulant. The metal nanoparticle core 12 could itself be a core-shell particle, hollow particle, or contain two or more materials in a well-defined or non-defined geometric orientation. Details concerning the use, manufacture and characteristics of a typical SERS nanotag are included in U.S. Pat. Nos. 6,514,767 and 7,192,778 entitled "Surface Enhanced Spectroscopy-Active Composite Nanoparticles," which patents are incorporated herein by reference. Although the invention is described in terms of SERS nanotags prepared from single nanoparticle cores 12, it is to be understood that nanoparticle core clusters or aggregates may be used in the preparation of SERS nanotags. Methods for the preparation of clusters of aggregates of metal colloids are known to those skilled in the art. The use of sandwich-type particles as described in U.S. Pat. No. 6,861,263, is also contemplated, which patent is incorporated herein by reference.

The nanoparticle core 12 may be of any material known in the art to be Raman-enhancing. The nanoparticle cores 12 may be isotropic or anisotropic. Anisotropic nanoparticles may have a length and a width. The particle 12 could comprise a collection of two or more particles of the same or different size, or the same or different shape, or mixtures of sizes and shapes. In some embodiments, the length of an anisotropic nanoparticle is the dimension parallel to the aperture in which the nanoparticle was produced. In the case of anisotropic nanoparticles, in some embodiments, the nanoparticle has a diameter (width) of 350 nm or less. In other embodiments, the nanoparticle has a diameter of 250 nm or less and in some embodiments, a diameter of 100 nm or less. In some embodiments, the width is between 15 nm to 300 nm. In some embodiments, the nanoparticle has a length of about 10-350 nm.

Nanoparticles suitable to be the core of a SERS nanotag include colloidal metal, hollow or filled nanobars, magnetic, paramagnetic, conductive or insulating nanoparticles, synthetic particles, hydrogels (colloids or bars), and the like. The nanoparticles used in the present invention can exist as single nanoparticles, or as clusters or aggregates of the nanoparticles.

It will be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. Another class of nanoparticles that has been described includes those with internal surface area. These include hollow particles and porous or semi-porous particles. Moreover, it is understood that methods to prepare particles of these shapes, and in certain cases to prepare SERS-active particles of these shapes, have been described in the literature. While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle.

A nanoparticle also includes a nanoparticle in which the metal includes an additional component, such as in a core-shell particle. For example, Ag core/Au shell particles, like those described in J. Am. Chem. Soc. 2001, 123, 7961, or Au core/Ag shell particles, or any core-shell combination involving SERS-active metals, can be used. Other combinations suitable for use in core-shell particles are included in this invention, such as Au- or Ag-nanoparticle functionalized silica/alumina colloids, Au- or Ag-functionalized $TiO_2$ colloids, Au nanoparticle capped-Au nanoparticles (see, for example, Mucic, et al., J. Am. Chem. Soc. 1998, 120, 12674), Au nanoparticle-capped. $TiO_2$ colloids, particles having and Si core with a metal shell ("nanoshells"), such as silver-capped $SiO_2$ colloids or gold-capped $SiO_2$ colloids. (See, e.g. Jackson, et al., 2004 Proc Natl Acad Sci USA. 101(52):17930-5; Talley, et al., *Nano Letters* (2005)). Hollow nanoparticles such as hollow nanospheres and hollow nanocrystals may also be utilized in the SERS nanotags.

Those skilled in the art will recognize that SERS nanotags can be formed on other, non-SERS active particles. For example, SERS-active metal nanoparticles can be immobilized on a silica particle. Reporters can be introduced, and the resulting particle can be silica-encapsulated.

Each SERS nanotag is encoded with a unique reporter 16, comprising an organic or inorganic molecule at the interface between the nanoparticle core and shell of glass or other suitable encapsulant. This approach to detection tags leverages the strengths of Raman scattering as a high-resolution molecular spectroscopy tool and the enhancements associated with SERS, while bypassing the shortcomings often encountered when making stand alone SERS substrates such as difficult reproducibility and lack of selectivity. The unique reporter 16 could comprise combinations of molecule (providing a more complex spectrum). Different tags could be made by varying the ratio of two (or more) reporters. SERS nanotags exhibit intense spectra (enhancement factors in excess of $10^6$) with the 633 and 785 nm excitation wavelengths that are excellent for avoiding intrinsic background fluorescence in biological samples such as whole blood and in matrices like glass and plastic. The silica coating, which is essentially SERS-inactive, stabilizes the particles against aggregation, prevents the reporter from diffusing away, prevents competitive adsorption of unwanted species, and provides an exceptionally well-established surface to which biomolecules can be conjugated for bioassay development (Aslam and Dent (1998) *Bioconjugation: Protein Coupling Techniques for the Biomedical Sciences*. Grove's Dictionaries Inc, New York, N.Y.). In other embodiments, encapsulants with some SERS activity can be used (and subtracted out from the Raman spectum), as long as they don't interfere with the spectrum of the reporter molecule.

Figure 2:
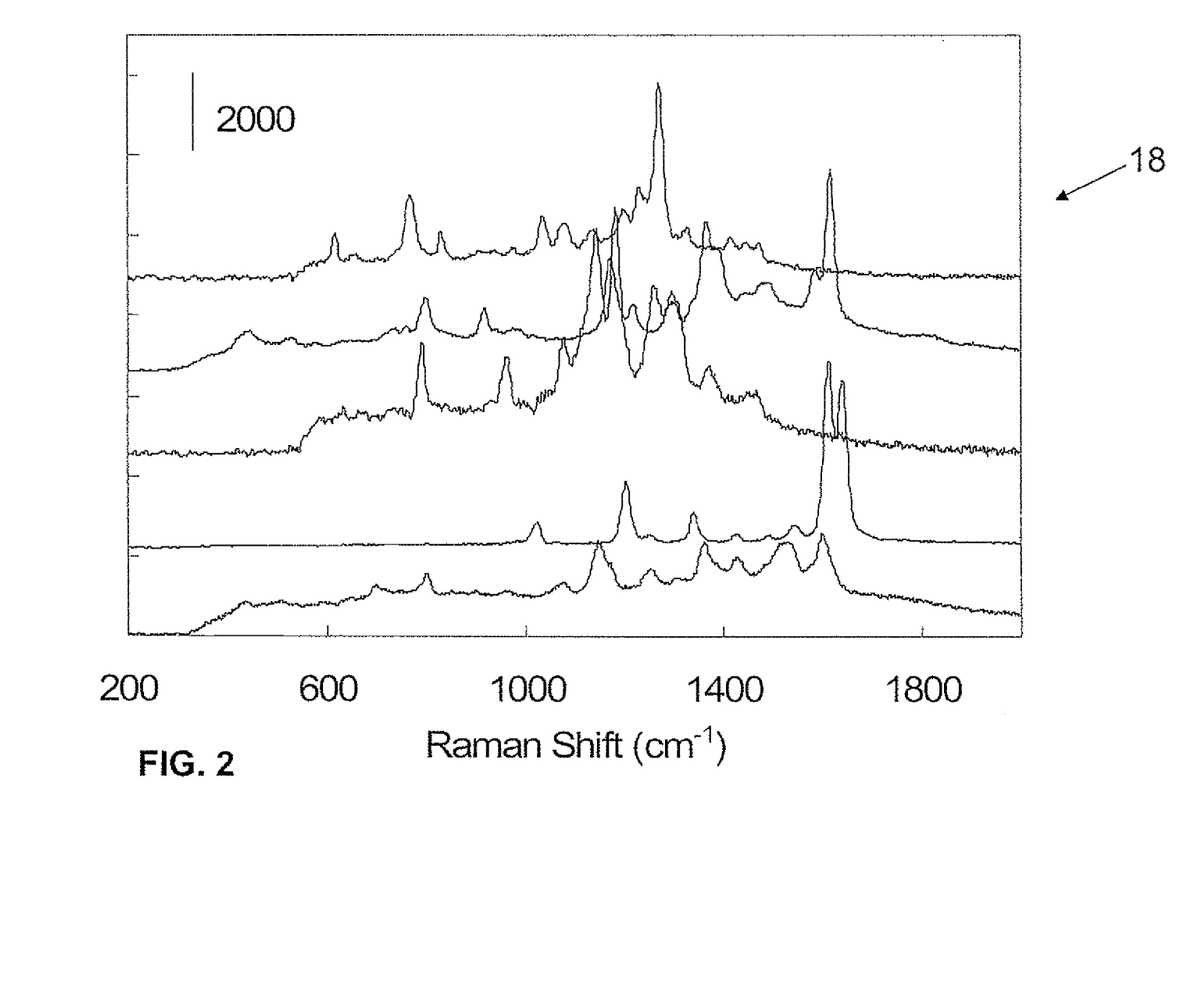
FIG. 2 is a graph comparison of the SERS spectra of SERS nanotags having five different reporter molecules.

Multiple unique flavors of tags are available. FIG. 2 shows a graph 18 of the spectra of five unique SERS tags, with clearly differentiated features, which can be utilized for a multiplexed assay. In a multiplexed assay, a single spectrum will be acquired, and it will be necessary to quantitatively separate that spectrum into its components. For spectra unmixing and quantification of the individual components an enhanced commercial software package may be used to carry out a linear least squares analysis using pure spectra from each tag as a standard.

The unique features of a SERS tag as described above render the particles particularly well suited for use as the reporter or indicator tags for any and all types of biological, chemical or diagnostic assays. A non-exclusive description of various types of assays which may be implemented with SERS tags follows. The following description contains only a representative list of assays suitable for implementation with SERS tags and is not intended to be limiting upon the scope of this invention. Those skilled in the art will readily appreciate that many other types of assay may be implemented utilizing SERS nanotags as reporter or indicator tags.

II. Assay Examples

Competitive Immunoassay

An immunoassay assay takes advantage of the specific binding of an antibody to its antigen. Monoclonal antibodies are often used as they only usually bind to one site of a particular molecule, and therefore provide a more specific and accurate test, which is less easily confused by the presence of other molecules. The antibodies picked must have a high affinity for the antigen (if there is antigen available, a very high proportion of it must bind to the antibody).

Both the presence of antigen or antibodies can be measured. For instance, when detecting infection the presence of antibody against the pathogen is measured. For measuring hormones such as insulin, the insulin acts as the antigen.

For numerical results, the response of the fluid being measured must be compared to standards of a known concentration. This is usually done though the plotting of a standard curve on a graph, the position of the curve at response of the unknown is then examined, and so the quantity of the unknown found. Detecting the quantity or presence of an antibody or antigen can be achieved by a variety of methods. For example, either the antibody or antigen can be conjugated with or otherwise labeled with a SERS nanotag. The Raman spectrum of the reporter molecule associated with the SERS nanotag may be detected as described above.

In a competitive immunoassay, the antigen in the unknown sample competes with labeled antigen to bind with antibodies. The amount of labeled antigen bound to the antibody site is then measured. In this method, the response will be inversely proportional to the concentration of antigen in the unknown. This is because the greater the response, the less antigen in the unknown was available to compete with the labeled antigen. The antigen may be labeled with a SERS nanotag.

Sandwich Immunoassay

In "sandwich" immunoassays, also referred to as non-competitive assays antigen in the unknown is bound to the antibody site, then labeled antibody is bound to the antigen. The antibody may be labeled with one or more SERS nanotags. The amount of labeled antibody on the site is then measured. Unlike the competitive method, the results of the noncompetitive method will be directly proportional to the concentration of the antigen. This is because SERS nanotag labeled antibody will not bind if the antigen is not present in the unknown sample.

Immunoassays can be homogeneous or heterogeneous. A heterogeneous immunoassay will require an extra wash step to remove unbound antibody or antigen from the site. Homogenous immunoassays, also known as no-wash assays have no wash step and detection takes place in the presence of unbound antibody or antigen. Because homogeneous assays do not require a wash step, they are typically faster and easier to perform. Homogenous assays may be less accurate or less easy to read due to the presence of unbound antibody or antigen.

Enzyme Immunoassay

An Enzyme-Linked ImmunoSorbent Assay, or ELISA, is a biochemical technique used mainly in immunology to detect the presence of an antibody or an antigen in a sample. It uses two antibodies. One antibody is specific to the antigen. The other reacts to antigen-antibody complexes, and is coupled to an enzyme. This second antibody, which accounts for "enzyme-linked" in the test's name, can be conjugated to or otherwise linked to a SERS nanotag to produce a detectable signal. Because the ELISA can be performed to evaluate either the presence of antigen or the presence of antibody in a sample, it is a useful tool both for determining serum antibody concentrations (such as with the Human Immunodeficiency Virus, HIV test or West Nile Virus) and also for detecting the presence of antigen. ELISA has direct and indirect variations. Sandwich and competitive variations of the basic ELISA are also known. All can be implemented with SERS nanotags as the detection/reporter modality.

Latex Agglutination Assay

A typical latex agglutination assay includes providing a reagent system having more than one particle which has the capacity to form multiple-particle aggregates and which bear on their surface(s) a ligand which is the same as or different than the ligand suspected to be present in the sample. At least one of the particles may be a SERS nanotag. The reagent system also includes an amount of receptor which is specific for both the ligand in the sample and the ligand borne on the particles. The amount of receptor should be sufficient to stabilize the particles.

Typical latex agglutination methods further include forming a test mixture by contacting the reagent system with the sample and passing the test mixture through a filter having apertures which are larger than the particles but smaller than the aggregates, thereby producing a filtrate. Any SERS nanotags bound in the filtrate or passed through the filter may then detected for the presence or absence of the ligand-bearing particles. The absence of ligand in the sample is confirmed by the presence of ligand-bearing particles in the filtrate, while presence of ligand in the sample is confirmed by the absence of ligand-bearing particles in the filtrate.

Protein-Protein and Protein-Ligand Assays

A wide variety of protein-based assays are possible that do not make use of antibodies. For example, protein-protein and protein-ligand assays are extraordinarily common in the drug discovery and drug development, all the way through to drug manufacture. SERS nanotags can easily be used in these types of assays, in a variety of formats, including but not limited to particle-particle and particle-surface modes.

Gel Electrophoresis

Gel electrophoresis is an separation assay method that separates macromolecules, typically nucleic acids or proteins, on the basis of size, electric charge, and other physical properties. A gel is a colloid in a solid form. The term electrophoresis describes the migration of charged particle under the influence of an electric field. Electro refers to the energy of electricity. Phoresis, from the Greek verb phoros, means "to carry across." Thus, gel electrophoresis refers to a technique in which molecules are forced across a span of gel, motivated by an electrical current. Activated electrodes at either end of the gel provide the driving force. A molecule's properties determine how rapidly an electric field can move the molecule through a gelatinous medium.

Many important biological molecules such as amino acids, peptides, proteins, nucleotides, and nucleic acids, posses ionisable groups and, therefore, at any given pH, exist in solution as electrically charged species either as cations or anions. Depending on the nature of the net charge, the charged particles will migrate either to the cathode or to the anode.

Gel electrophoresis is a separation technique. After the electrophoresis runs, when molecules have almost reached the cathode or anode, the molecules in the gel are traditionally stained to make them visible. However, SERS nanotags can be bound or conjugated to select molecules separated with this technique to provide an alternative detection modality. Typically, gel electrophoresis is followed by a specific detection routine such as the blot techniques described immediately below.

Western Blot

A western blot is used to detect a large molecule, typically protein in a given sample of tissue homogenate or extract. Gel electrophoresis or another suitable separation technique is used to separate native proteins by shape and/or size. The proteins are then transferred out of the gel and onto a membrane (typically nitrocellulose or PVDF). Subsequently, researchers can examine the size, processing, or amount of protein in a given sample and compare several groups.

During the detection process the membrane is "probed" for the protein of interest with a modified antibody. Traditionally, the modified antibody is linked to a reporter enzyme, which when exposed to an appropriate substrate drives a colorimetric reaction and produces a color. The modified antibody may however be bound or conjugated with a SERS nanotag which may be detected through a Raman spectrum as described above. For a variety of reasons, the detection step traditionally takes place in a two-step process, although there are now one-step detection methods available for certain applications. SERS nanotags may be suitable detection means in either case.

Usually, unbound probes are washed away and the western blot is then ready for detection of the probes that are labeled and bound to the protein of interest. In practical terms, not all westerns reveal protein only at one band in a membrane. Traditionally, size approximations were taken by comparing the stained bands to that of the marker or ladder loaded during electrophoresis. Colorimetric measurement has been used to evaluate the intensity of a traditional blot stain. All traditional measurements can be enhanced by using SERS nanotags as reporters and examining the quality and intensity of the SERS spectrum obtained as described above.

Southern Blot

A Southern blot is routinely used in molecular biology to check for the presence of a DNA sequence in a DNA sample. Southern blotting generally combines agarose gel electrophoresis for size separation of DNA with methods to transfer the size-separated DNA to a filter membrane for probe hybridization. The method is named after its inventor, the British biologist Edwin Southern. The probe may include a SERS nanotag for enhanced detection capabilities.

The steps included in the preparation and examination of a Southern blot generally include cutting high-molecular-weight DNA strands into smaller fragments with restriction endonucleases or another method. The DNA fragments are then separated by size by electrophoreses on an agarose gel. If some of the DNA fragments are larger than 15 kb, the gel may be treated with an acid, such as dilute HCl, which depurinates the DNA fragments, breaking the DNA into smaller pieces, thus allowing more efficient transfer from the gel to membrane.

A sheet of nitrocellulose (or, alternatively, nylon) membrane is placed into contact with the gel. Pressure is applied evenly to the membrane to ensure good and even contact between gel and membrane. Buffer transfer by capillary action is then used to move the DNA from the gel on to the membrane; ion exchange interactions bind the DNA to the membrane due to the negative charge of the DNA and positive charge of the membrane.

The membrane may then be baked, (in the case of nitrocellulose) or exposed to ultraviolet radiation (nylon) to permanently and covalently crosslink the DNA to the membrane.

The membrane is then exposed to a hybridization probe, typically a single DNA fragment with a specific sequence whose presence in the target DNA is to be determined. In some cases, the hybridization probe may be made from RNA, rather than DNA. The probe may be labeled with SERS nanotags so that it can be detected using the techniques described above. After hybridization, excess probe is washed from the membrane, and the Raman spectrum of bound tags may be detected.

Northern Blot

A northern blot is technically similar to the Southern blot described above, however RNA, rather than DNA, is the substance being analyzed by electrophoresis and detection with a hybridization probe. A notable difference in the procedure (as compared with the Southern blot) is the addition of formaldehyde in the agarose gel, which acts as a denaturant. As in the Southern blot, the hybridization probe may be made from DNA or RNA. The hybridization probe may include SER nanotag markers.

A variant of the procedure known as the reverse northern blot is sometimes used. In this procedure, the substrate nucleic acid (that which is affixed to the membrane) is a collection of isolated DNA fragments, and the probe is RNA extracted from a tissue and labeled. As described above, the probe may be labeled with one or more SERS nanotags. Other blot techniques are known or in development. It is likely that all can be implemented with SERS nanotags bound to the detection probe.

Chromatography

Chromatography is the collective term for a family of laboratory techniques for the separation of mixtures. Chromatography involves passing a mixture dissolved in a "mobile phase" through a stationary phase, which separates the analyte to be measured from other molecules in the mixture and allows it to be isolated. Numerous types of chromatography are commonly employed including but not limited to the following: Column chromatography, planar chromatography, paper chromatography, thin layer chromatography, gas chromatography, liquid chromatography, supercritical fluid chromatography, ion exchange chromatography, size exclusion chromatography, affinity chromatography, reversed-phase chromatography, two-dimensional chromatography, pyrolysis gas chromatography, fast protein liquid chromatography, countercurrent chromatography and others.

Chromatography may be preparative or analytical. Preparative chromatography seeks to separate the components of a mixture for further use (and is thus a form of purification). Analytical chromatography normally operates with smaller amounts of material and seeks to measure the relative proportions of analytes in a mixture. The two are not mutually exclusive. In either case SERS nanotags may be bound to a probe to interrogate an analyte, or bound directly to an analyte. The SERS nanotags may then be detected using the techniques described above.

Mass Spectrometry

Mass spectrometry is an analytical technique used to measure the mass-to-charge ratio of ions. It is most generally used to find the composition of a physical sample by generating a mass spectrum representing the masses of sample components. Mass spectrometry is an important emerging method for the characterization of proteins and other large molecules. The two primary methods for ionization of whole proteins are electrospray ionization (ESI) and matrix-assisted laser desorption/ionization (MALDI). In keeping with the performance and mass range of available mass spectrometers, two approaches are used for characterizing proteins. In the first, intact proteins are ionized by either of the two techniques described above, and then introduced to a mass analyser. In the second, proteins are enzymatically digested into smaller peptides using an agent such as trypsin or pepsin. Other proteolytic digest agents are also used. The collection of peptide products are then introduced to the mass analyser. This is often referred to as the "bottom-up" approach of protein analysis.

Proteins of interest to biological researchers are usually part of a very complex mixture of other proteins and molecules that co-exist in the biological medium. This presents two significant problems. First, the two ionization techniques used for large molecules only work well when the mixture contains roughly equal amounts of constituents, while in biological samples, different proteins tend to be present in widely differing amounts. If such a mixture is ionized using electrospray or MALDI, the more abundant species have a tendency to "drown" signals from less abundant ones. The second problem is that the mass spectrum from a complex mixture is very difficult to interpret due to the overwhelming number of mixture components. This is exacerbated by the fact that enzymatic digestion of a protein gives rise to a large number of peptide products.

Several recent methods allow for the quantization of proteins by mass spectrometry. Historically, stable (e.g. non-radioactive) heavier isotopes of carbon (C13) or nitrogen (N15) are incorporated into one sample while the other one is labeled with corresponding light isotopes (e.g. C12 and N14). The traditional labels associated with quantitative mass spectrometry can be different flavors of SERS nanotags. The two samples are typically mixed before the analysis. Peptides derived from the different samples can be distinguished due to their mass difference and quantitatively compared using the methods for interrogation of SERS nanotags described above. The use of SERS nanotags may similarly enhance numerous other mass spectrometry techniques not described in detail herein.

Protein Arrays or Chips

Protein arrays are solid-phase ligand binding assay systems using immobilized proteins on surfaces which include glass, membranes, microliter wells, mass spectrometer plates, and beads or other particles. The assays are highly parallel (multiplexed) and often miniaturised (such as microarrays, protein chips). Their advantages include being rapid and automatable, capable of high sensitivity, economical on reagents, and providing an abundance of data for a single experiment. Bioinformatics support is important; the data handling demands sophisticated software and data comparison analysis. One of the chief formats is the capture array, in which ligand-binding reagents, which are usually antibodies but may also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays will be used to quantitate and compare the levels of proteins in different samples in health and disease, i.e. protein expression profiling, and in this the protein arrays may challenge 2DE technology. Proteins other than specific ligand binders are used in the array format for in vitro functional interaction screens such as protein-protein, protein-DNA, protein-drug, receptor-ligand, enzyme-substrate, etc. They may also be used to correlate the polymorphic changes resulting from SNPs with protein function. The capture reagents themselves will need to be selected and screened against many proteins, which can also be done in a multiplex array format against multiple protein targets.

Thus, broadly speaking, there are at least four major areas where protein arrays are being applied, each of which requires appropriate formats and readout methods. The broad areas include;

Diagnostics: detection of antigens and antibodies in blood samples; profiling of sera to discover new disease markers; environment and food monitoring.

Proteomics: protein expression profiling; organ and disease specific arrays.

Isolation of individual members from display libraries for further expression or manipulation: selection of antibodies and protein scaffolds from phage or ribosome display libraries for use in capture arrays.

Protein functional analysis: protein-protein interactions; ligand-binding properties of receptors; enzyme activities; antibody cross reactivity and specificity, epitope mapping.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Fluorescence labeling and detection methods are traditionally used with protein arrays. For example, for differential display, capture (e.g. antibody) arrays can be probed with fluorescently labeled proteins from two different cell states, in which cell lysates are directly conjugated with different fluorophores and mixed. A similar detection strategy could be implemented with SERS nanotags as the detection modality. The proteins from each cell state for example could be labeled with distinct flavors of SERS tags which are then detected as described above. Related microarray technologies which may be implemented using SERS nanotags include but are not limited to DNA microarrays, Antibody microarrays, Tissue microarrays, Cell microarays and Chemical Compound Microarrays.

Flow Cytometry

Flow cytometry is a technique for counting, examining and sorting microscopic particles suspended in a stream of fluid. It allows simultaneous multiparametric analysis of the physical and/or chemical characteristics of single cells flowing through an optical and/or electronic detection apparatus. A typical flow cytometer includes a light source, generally a laser light source, aimed at the cytometry flow.

Traditionally, each suspended particle passing through the beam scatters the light in some way, and fluorescent chemicals found in the particle or attached to the particle may be excited into emitting light at a lower frequency than the light source. This combination of scattered and fluorescent light is picked up by the detectors, and by analysing fluctuations in brightness at each detector (one for each fluorescent emission peak) it is then possible to extrapolate various types of information about the physical and chemical structure of each individual particle. SERS nanotags may be associated with the particles suspended in the stream of fluid. In this case the traditional flow cytometry measurements may be made along with supplemental interrogation of the SERS tags as described above. SERS nanotags may similarly be used to enhance flow cytometry based cell sorting and similar related techniques. Skilled practitioners will recognize that SERS nanotags can be used with a variety of other cytometry techniques, including microvolume laser scanning cytometry. In addition, SERS tags can be coupled with non-cytometry-based methods of cell sorting and/or separation. For example, single cells can be sorted in lithographically-generated devices that control the direction and rate of flow.

Microfluidic Assays

A wide variety of assays employ microfluidics to control and/or miniaturize flowing streams. SERS nanotags can be incorporated into microfluidic assays in a variety of means. In one example, SERS nanotags are introduced into a sample using microfluidics. In another, a sample is separated into components by microfluidic methods, with SERS nanotags added to one or more components. Microfluidics can be used to separate species with SERS nanotags bound to them from species that do not. Such species might be molecules, polymers, cells, or particles. For example, a sandwich immunoassay can be performed using a latex bead with a capture antibody and a SERS nanotag with a detection antibody. The microfluidic device can separate latex beads that have SERS nanotags bound (by virtue of the presence of antigen) from those that do not have bound SERS tags. In addition, the separated bead-nanotag complexes can be concentrated using microfluidics.

Other Optical Assays

SERS nanotags can be used in conjunction with other optical techniques that are used in biology, chemistry, engineering, materials science, diagnostics, and/or medicine. For example, optical tweezers are used to trap and/or study one or more species (particles, cells, objects). SERS nanotags can also be captured by tweezers; alternatively, SERS nanotags can be interrogated when bound to species that have been trapped by optical tweezers. Likewise, SERS nanotags can be detected by a variety of multi-photon techniques in an assay format. For example, surface enhanced hyperRaman can be used to develop optical background free assays using SERS nanotags. Here, one might use two 1500 nm photons, and detect the Raman shifted photon at 750 nm. Alternatively, it may be possible to use coherent detection methods (e.g. CARS) in assays.

Also, a variety of other optical techniques can be used in conjunction with SERS. For example, light scattering can be measured from SERS tags as a screen to detect the presence or absence of particles. Then SERS measurements can be carried out to determine the identity the particle. Such a method could be very useful in high throughput screening, as it allows the presence of particles to be very quickly determined. Likewise, this method can be used in lateral flow or other types of immunochromatographic assays, where detection of particles is first carried out by eye based on scattered light, and followed up by an instrument-based SERS readout to quantify the number and types of SERS nanotags.

Reduced Background Proximity Assays

A novel assay method involving SERS-active particles (including but not limited to SERS nanotags) is based upon the exploitation of the emission of Raman photons at particular frequencies to stimulate other processes. In many bioassay formats, the ultimate assay sensitivity is limited by background signal due to non-specific binding and/or other factors. Accordingly, assay formats that are able to produce "background-free" or reduced background signals are highly advantageous. A good example of this involves two-photon fluorescent processes, where an assay utilizes two photons of wavelength 1000 nm to stimulate an emission process detected at wavelengths beyond 500 nm. Since no 500 nm photons are input, potential background fluorescence at the detection frequency in biological samples, glassware, etc. is avoided.

Another type of useful assay relies upon signal generation only when two or more) components are brought together. A variety of these assays, generally called proximity assays, exists. For example, in complementation assays, a fluorescent protein is split into two parts, and each part is attached to a different molecule (e.g. A and B). When A and B are apart, fluorescence is not possible. However, when A and B are in close proximity (i.e. bound to one another), the fragments of the fluorescent protein are close enough to re-assemble into a functional protein, and optical excitation leads to emission. Thus, the detection of a fluorescent photon is coupled to formation of the A:B complex.

A potentially more advantageous assay incorporates the concepts of both reduced background and proximity assays. For example, the generation of a detectable photon at a frequency where there is no background noise as a result of a proximate binding event. The plasmonic attributes of SERS-active nanoparticles as described herein allows such an assay format to be implemented.

It is well understood that excitation of nanoparticle plasmons are strongly coupled to SERS activity. The two most common types of SERS-active nanoparticles are Au and Ag. Spherical Au colloidal particles typically exhibit plasmon resonances in the 520-560 nm range, depending on diameter, while spherical Ag nanoparticles can exhibit resonances in the 400-450 nm range, again depending on particle size. It is moreover well known that the enhancement in Raman intensity associated with SERS goes up significantly when the plasmon involves two or more particles in close proximity (e.g. dimers, trimers, or aggregates). Specific examples of SERS active particles with tunable plasmon responses are described in detail below.

For example, it has been demonstrated that gold nanorods of aspect ratio 1.5 to 10 will have corresponding absorption maxima from 600 to 1300 nm (Nikoobakht, B; El-Sayed, M A. "Preparation and growth mechanism of gold nanorods (NRs) using seed-mediated growth method" CHEMISTRY OF MATERIALS, 15 (10): 1957-1962 May 20, 2003). Similarly, gold nanorods with aspect ratios of up to 23 have been grown. (Gole, A; Murphy, C J "Seed-mediated synthesis of gold nanorods: Role of the size and nature of the seed" CHEMISTRY OF MATERIALS, 16 (19): 3633-3640 Sep. 21, 2004). It has also been demonstrated that silver nanoprisms may be grown through novel illumination methods such that the resulting nanoprisms have edge-lengths from 38-120 nm and absorption bands ranging from 470-1000 nm (Jin, R C; Cao, Y C; Hao, E C; et al. "Controlling anisotropic nanoparticle growth through plasmon excitation" NATURE, 425 (6957): 487-490 Oct. 2, 2003). Also, it has been shown that wet chemical methods may be used for synthesis of gold prisms with edge lengths of 100-300 nm and absorption bands past 1200 nm (Millstone, J E; Metraux, G S; Mirkin, C A "Controlling the edge length of gold nanoprisms via a seed-mediated approach" ADVANCED FUNCTIONAL MATERIALS, 16 (9): 1209-1214 Jun. 6, 2006).

Silver nanocubes may be produced and used as sacrificial templates for gold "nanoboxes" (Sun, Y G; Xia, Y N "Shape-controlled synthesis of gold and silver nanoparticles" SCIENCE, 298 (5601): 2176-2179 Dec. 13, 2002). Methods exist for tuning the plasmon resonance of nanoparticles in the visible spectrum (Sun, Y G; Xia, Y N "Gold and silver nanoparticles: A class of chromophores with colors tunable in the range from 400 to 750 nm" ANALYST, 128 (6): 686-691 2003). More recently, the synthesis of silver nanobars and "nanorice" has been shown, which particles have plasmon resonances extending out to nearly 900 nm (Wiley, B J; Chen, Y C; McLellan, J M; et al. "Synthesis and optical properties of silver nanobars and nanorice" NANO LETTERS, 7 (4): 1032-1036 April 2007).

Similar methods have been used to create hollow gold particles with absorption maxima ranging from 400-990 nm using silver nanospheres as sacrificial templates (Alvarez-Puebla, R A; Ross, D J; Nazri, G A; et al. "Surface-enhanced Raman scattering on nanoshells with tunable surface plasmon resonance" LANGMUIR, 21 (23): 10504-10508 Nov. 8, 2005). Small, monodisperse hollow gold shells with absorption maxima around 600 nm have been produced using cobalt nanoparticles as a precursor (Schwartzberg, A M; Oshiro, T Y; Zhang, J Z; et al. "Improving nanoprobes using surface-enhanced Raman scattering from 30-nm hollow gold particles" ANALYTICAL CHEMISTRY, 78 (13): 4732-4736 Jul. 1, 2006). Elegant methods are known for coating gold onto a silica core, yielding intense plasmon resonances extending from the far-red to 2200 nm (Oldenburg, S J; Jackson, J B; Westcott, S L; et al. "Infrared extinction properties of gold nanoshells" APPLIED PHYSICS LETTERS, 75 (19): 2897-2899 Nov. 8, 1999). Other methods of producing SERS-active nanoparticles with tunable Plasmon responses are known or will be developed in the future. Some or all of these types of particles may be useful in implementing the novel spectra and assays described herein.

Figure 3:
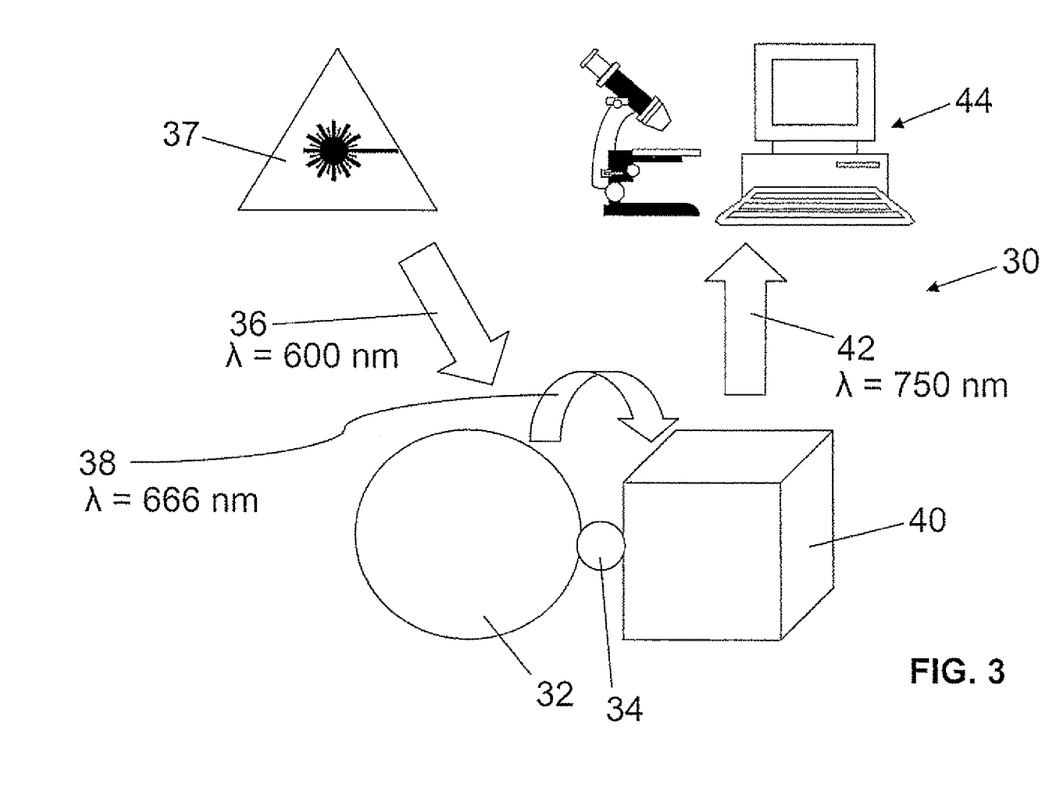
FIG. 3 is a schematic diagram of a proximity assay embodiment featuring two types of SERS-active nanotags.

Description of the Assay:

A SERS-active proximity assay may be designed with particles having any suitable plasmon characteristics. The prophetic examples described below are non-limiting. A representative non-limiting example of a proximity assay 30 is schematically depicted in FIG. 3. This representative assay includes a first SERS-active particle 32 with a surface plasmon maximum at 600 nm, or 16,666 cm$^{-1}$. Adsorbed to it or in very close proximity is a molecule 34 with an intense Raman band at 1666 cm$^{-1}$. The particle/molecule is irradiated using monochromatic 600 nm light 36 from a laser 37. The Stokes-shifted photon 38 emitted from this system in a Raman experiment will be at 16,666-1,666, or 15,000 cm$^{-1}$, which is equivalent to a wavelength of 666 nm. The intensity of the emitted photon 38 will be greater than in a typical Raman experiment by virtue of the single-particle SERS effect: depending on the shape and composition, enhancements of $10^4$ to $10^7$ might be expected.

The representative assay 30 also includes a second SERS-active particle 40, which is brought adjacent to the first, with the molecule 34 sandwiched in between. The second particle has a sharp surface plasmon peak at 666 nm. The laser excitation at 600 nm does not excite SERS from this second particle. However, the Raman-shifted photon 38 from the first particle 32 does, since it corresponds precisely to the absorbance maximum. The Stokes-shifted photon 42 emitted from the second particle (because it is also in close proximity to the molecule 34) will occur at 15,000-1,666, or 13,334 cm$^{-1}$, or 750 nm. Thus, in this system, excitation at a single wavelength (600 nm) leads to emission at two different wavelengths, 666 and 750 nm, corresponding to the difference between the input photon energy and once and twice the vibrational frequency, respectively. The emission at 750 nm may be detected with a detector 44 and the detected signal will have reduced background noise characteristics. It is important to note that the excitation wavelength and emission wavelengths described above are representative and non-limiting examples only. However, the relationship between the excitation wavelength and emission wavelength may be generalized. In particular, if the reporter used possesses a SERS-active vibrational peak at energy v1, detection may be accomplished at a frequency L-(2v1) where L is the laser excitation frequency.

Functional assays may be prepared where the two nanoparticles have absorbance maxima separated by any suitable amount. Particles having absorbance maxima separated by approximately 200 cm$^{-1}$ and 3500 cm$^{-1}$ are particularly well suited to the implementation of proximity assays as described herein. As is described in detail above, particles having suitably separated and specifically tailored absorbance maxima may be prepared by having two types of nanoparticles with different shapes. For example, one particular may be spherical and the other non-spherical. Alternatively, the first particle may be solid and the second hollow. The first particle may be of uniform composition with the second particle having a different composition or structure such as a core and shell. The absorbance characteristics of the particles may also be affected by the materials selected for each particle. For example, one particle may be fabricated from a single metallic element and the other particle from a mixture, alloy or different metal. For example, a first particle may be of Au and the second of Ag. Either particle may be an alloy or mixture of Au, Ag or other elements, compositions or materials.

A convenient way to engineer an assay such as is described with respect to FIG. 3 is to carry out a sandwich assay using either DNA or proteins. For example, in a sandwich immunoassay, the first particle 32 can be covered with a capture antibody (Ab), and the second particle 40 can be covered with a detection Ab. If either Ab is modified with a SERS-active reporter (i.e., molecule 34), when a sandwich is formed by the presence of an antigen, it will necessarily bring the SERS-active reporter in between the particles. Alternatively, one can use particles in which part of the surface of the SERS-active particles are covered with an adsorbed reporter molecule, and part is covered with an Ab.

It is well-understood that Raman cross sections, even with SERS, are small, and so using the representative example discussed above, the number of 750 nm photons emitted will be small compared to the number of 666 nm photons emitted. Nevertheless, the background signal at 750 nm will be very small or zero compared to what it would be at 666 nm.

Moreover, the assay may be arranged in a way to maximize the number of 750 nm photons generated, as follows. Rather than introducing a mixture of both types of Ab-clad particles to a sample containing an analyte, in this assay it may be advantageous to have the analyte bind initially to the Ab associated with the first particle. Then, introduction of the second particle leads to sandwich formation, but with the second particle completely surrounding the first. This is optimal because the first particle will emit 666 nm photons around 4 pi steradians (i.e. in all space). Ideally, having the second particle completely surrounding the first particle in three dimensions maximizes the probability of a Raman scattering event generating a photon at 750 nm.

In summary, a novel proximity assay may be prepared or implemented as described above. It is important to note that the representative photon characteristics described herein are not limiting. The energy levels and wave characteristics of the detected energy will be determined by the physical characteristics of the particles and the reporter and as described above may be fine tuned by fabricating particles from selected materials having a selected shape, size and surface structure. For example, if a SERS nanoparticle A absorbs a photon at 13,000 cm$^{-1}$, and emits a Raman photon at 11,700 cm$^{-1}$, and SERS nanoparticle B is excited at 11,700 cm$^{-1}$ (but not at 13,000 cm$^{-1}$) and emits a scattered photon at 10,000 cm$^{-1}$, one could in principle excite a collection of particles of A and B at 13,000 cm$^{-1}$ and detect photons just at 10,000 cm$^{-1}$. In practice, such a phenomenon will occur at detectable levels only when the particles are efficient scatterers, efficient absorbers, and most importantly, are very close to one another. Thus, appropriately designed pairs of SERS nanotags can be used in a variety of proximity assays, where binding or de-binding of Species 1 to Species 2 can be detected by the appearance or loss of a particular SERS signal.

Another type of proximity assay leverages the fact that electromagnetic field enhancements that drive SERS can often be orders of magnitude larger in between very closely spaced particles than at single particles. Thus, detection levels can be set such that SERS signals from individual particles are not detected, but SERS signals from closely spaced particles can be detected. In such an instance, the molecule detected could be the reporter at the surface of one or both SERS-active particles, in which case the proximity assay yields a more intense (and thus detectable) spectrum of the reporter. Alternatively, the detection levels can be adjusted so that the SERS of the reporters at individual particles are detectable, and the particles are brought into close proximity with a molecule between the particles, one example being an antigen in a sandwich immunoassay. In such an instance, the SERS spectrum will change from that of the reporters to that of the reporters plus that of the antigen.

All these aforementioned types of proximity assays can be multiplexed, i.e. use of multiple reporters on multiple particles allows multiple analytes to be detected and/or quantitated.

Alternatively, SERS tags could be used in the context of a UV-vis or extinction assays. Immobilization of SERS nanotags in a small path length device (e.g. a thin layer cell) can be made by UV-vis, followed by SERS interrogation for quantitation.

Electrochemical Assays

SERS nanotags can be used in conjunction with electrodes and electrochemical methods. For example, SERS nanotags could be immobilized to a metal surface. The total number of tags bound could be determined by changes in capacitance of the electrode, while the number and identity of the tags can be determined by optical interrogation using SERS. Here, the capacitance is used to provide confirmation as to the number of particles bound. Alternatively, SERS nanotags could be bound to an electrode surface via one or more methods described above (e.g. an immunoassay). Then, the number and identity of the tags could be determined by SERS. Then, the particles could be electrochemically oxidized to provide a measure of metal content. Other electrochemical methods, including but not limited to potentiometric methods, coulometric methods, and voltammetric methods, can also be used.

Gravimetric and Other Assays

SERS nanotags can also be used in a variety of mass-sensing techniques. For example, quartz crystal gravimetry can be used to detect the presence of nanoparticles, followed by SERS interrogation. Alternatively, the more sensitive MEMS-based sensors and/or quartz or metal resonators that detect mass by differences in shear, or by other means, can be used to detect the presence of small numbers of SERS nanotags, with subsequent identification by Raman.

The electrochemical and gravimetric assays comprise "orthogonal methods" to detect the presence or absence or quantify the total number of SERS nanotags. While they do not provide spectral information (and thus cannot be used to multiplex), such methods could nonetheless be useful (e.g. for screening, for absolute quantitation, or for elimination of false positives). For example, an ultra sensitive assay could be developed based on the detection of a very small number of SERS nanotags, perhaps even a single particle. The parallel detection of that particle or particles by non-optical method provides significantly increases the confidence level of the measurement.

A variety of other orthogonal detection methods exist, including but not limited to atomic absorption and atomic emission, x-ray diffraction, x-ray scattering, neutron scattering, electron microscopy, atomic force microscopy, scanning tunneling microscopy, other scanned probe microscopies, and x-ray fluorescence.

SERS nanotags can also be detected using instruments other than Raman spectrometers. Thus, fluorimeters designed to read fluorescence can also detect SERS nanotags with reporters tuned to emit photons at the same wavelengths as fluorophore emission. In fact, with the appropriate filter sets, SERS nanotags can be detected with very inexpensive instrumentation.

III. Other Assay Formats and Marking Techniques

SERS nanotags can be used as markers, tags or detection modalities or otherwise in other types of assay not specifically described herein. For example SERS nanotags may be used in assays such as (but not limited to) the following:

Capillary Electrophoresis,
Dielectrophoresis,
Isoelectric Focusing,
Any other assay format.

In addition SERS nanotags may be used to implement cell or material labeling before any further assay steps such as separation. The SERS tags may be used in many cases without concern for the nature of the separation or other subsequent assay steps. One representative, non-exclusive example of initial marking includes applications such as in gene expression, multiplexed PCR labeling, SERS in situ hybridization, multiplexed pathogens detection, or even real time PCR. For example, SERS tags may be used to label patient RNA or DNA to replace known Cy5 and Cy3 fluorescent dyes in microarray gene expression. In another representative example, multiplexed SERS tag labeling primers may be used to amplify various viral RNAs and detect simultaneously viral pathogens.

In Situ Hybridization

In situ hybridization is a technology utilizing a labeled complementary DNA or RNA strand (i.e., probe) to localize a specific DNA (within the chromosomes of the nucleus) or RNA (within the cytoplasm) in a portion or section of tissue (in situ), or in the entire tissue (whole mount ISH). This is distinct from immunohistochemistry, which localizes proteins in tissue sections.

For hybridization, sample cells and tissues are usually treated to fix the target transcripts in place and to increase access of the probe. The probe hybridizes to the target sequence at elevated temperature, and then the excess probe is washed away. Solution parameters such as temperature, salt and/or detergent concentration can be manipulated to remove any non-specific hybridization. Then, the probe that was labeled is localized and quantitated in the tissue.

Traditionally, probes were radiolabelled with $^{32}P$ $^{35}S$ of $^3H$ but more recently non-radioactive labels have been developed which in general are more versatile. SERS nanotags can be one of the alternative labels which provide equal or greater sensitivity, produce quicker results generally, and also of importance, avoids the handling of hazardous materials.

SERS ISH Versus FISH (Fluorescence In Situ Hybridization)

The advent of fluorescent dyes for use as labels has made it possible to visualize multiple probes at the same time. The SERS nanotag as label provides even more advantages, such as higher level of mutiplexicity and greater sensitivity, has opened up new possibilities for investigating and diagnosing diseases. This includes but not limited to: to form a diagnosis, evaluate prognosis, to evaluate remission of a disease, such as cancer, or to identify the pathogen species and compare their genomes from small samples of patient's tissue. Treatment can then be specifically tailored.

In Situ PCR and In Situ RT-PCR

Conventional in situ hybridization has a limitation as to the number of copies of a sequence which can be resolved. One way to enhance the resolution of this technique has been to combine in situ hybridization with the very powerful technique of polymerase chain reaction. This has the potential of resolving a single copy of a gene sequence or low levels of cytoplasmic mRNA. It has proved to be particularly useful as a diagnostic tool for the detection and identification of cells infected with viral DNA. The probe may include a SERS nanotag for enhanced detection capabilities.

PRINS (PRimed In Situ Labeling)

PRINS is an alternative way to traditional in situ hybridization for the identification of chromosomes in metaphase spreads or interphase nuclei. This method provides rapid detection with less background noise. The denatured DNA is hybridized to short DNA fragments, or designed oligonucleotides. Primer extension is then carried out with the appropriate polymerase in the presence of labeled nucleotides. The labeled site can be detected using a suitable SERS nanotag conjugated antibody.

Recombinase Polymerase Amplification (RPA)

RPA is a DNA amplification technique which provides the advantage over the other DNA amplification methods. In RPA, the isothermal amplification of specific DNA fragments is achieved by the binding of opposing oligonucleotide primers to the template DNA and their extension by a DNA polymerase. The assay is rapid and sensitive. Little or no hardware is required to support and sustain the RPA process making it ideal for point-of-care and field applications. SERS nanotags in combination with magnetic beads can be applied to the assay to develop a SERS-RPA. In the assay, a biotinylated 5' primer and SERS tag conjugated 3' primer will bind to the specific target DNA. After RPA, the neutroavdine coated magnetic bead is added, then pull down the bead and acquire the signal. The SERS-RPA will be an ultra-sensitive and rapid diagnostic method for identifying human pathogens, GMC plant and for blood bank screening, and so on.

IV. Example Independent Separation Techniques

Certain of the assays described above utilize specialized separation steps such as gel electrophoresis prior to the detection of assay results. Many assays can be performed after an independent separation of the analyte from other components, for example a biological matrix. Any assay which includes a separation step can potentially be enhanced or performed with SERS nanotags attached, incorporated into or otherwise associated with a component of the analyte. Representative independent separation methods in addition to those discussed specifically above include but are not limited to the following: Filtration, centrifugation, tangential flow filtration, field flow fractionation, microfluidics, electrostatic separation, density gradient filtration, electrochemical separation, capillary electrophoresis; magnetic bead separation, and other mechanical, physical, chemical, electrical or biological separation techniques.

What is claimed is:

1. A method of producing a surface enhanced Raman scattering (SERS) spectrum comprising:
    providing a first SERS active nanoparticle which will absorb a photon at a first wavelength and emit a Raman shifted photon at a second wavelength that is different from the first wavelength;
    providing a second SERS active nanoparticle which will absorb a photon at the second wavelength and emit a Raman shifted photon at a third wavelength that is different from the first wavelength and the second wavelength;
    bringing the first and second SERS active nanoparticles proximate to one another;
    and illuminating the first SERS active nanoparticle at the first wavelength causing the first SERS active nanoparticle to emit a Raman shifted photon at the second wavelength which is absorbed by the second SERS active nanoparticle causing emission of a second Raman shifted photon at the third wavelength.

2. The method of producing a surface enhanced Raman scattering (SERS) spectrum of claim 1 wherein the first SERS active nanoparticle and the second SERS active nanoparticle have different shapes.

3. The method of producing a surface enhanced Raman scattering (SERS) spectrum of claim 2 wherein the first SERS active nanoparticle is spherical and the second SERS active nanoparticle is non-spherical.

4. The method of producing a surface enhanced Raman scattering (SERS) spectrum of claim 2 wherein the first SERS active nanoparticle is solid and the second SERS active nanoparticle is hollow.

5. The method of producing a surface enhanced Raman scattering (SERS) spectrum of claim 2 wherein the first SERS active nanoparticle is of uniform composition and the second SERS active nanoparticle has different compositions in a core and shell.

6. The method of producing a surface enhanced Raman scattering (SERS) spectrum of claim 2 wherein the first SERS active nanoparticle comprises a single metal and the second SERS active nanoparticle comprises a mixture or alloy of two metals.

7. The method of producing a surface enhanced Raman scattering (SERS) spectrum of claim 6 wherein the second SERS active nanoparticle comprises a mixture or alloy of Au and Ag.

8. The method of producing a surface enhanced Raman scattering (SERS) spectrum of claim 1 wherein an absorbance maximum of the first SERS active nanoparticle is separated from an absorbance maximum of the second SERS active nanoparticle by between 200 cm$^{-1}$ and 3500 cm.$^{-1}$.

9. A proximity assay comprising:
    a first SERS active nanoparticle which will absorb a photon at a first wavelength and emit a Raman shifted photon at a second wavelength;
    a second SERS active nanoparticle which will absorb a photon at the second wavelength and emit a Raman shifted photon at a third wavelength; and
    a light source configured to emit light at the first wavelength; and
    a detector configured to detect light at the third wavelength wherein the first, second and third wavelengths are different from one another.

10. The proximity assay of claim 9 wherein the first SERS active nanoparticle and the second SERS active nanoparticle have different shapes.

11. The proximity assay of claim 10 wherein the first SERS active nanoparticle is spherical and the second SERS active nanoparticle is non-spherical.

12. The proximity assay of claim 10 wherein the first SERS active nanoparticle is solid and the second SERS active nanoparticle is hollow.

13. The proximity assay of claim 10 wherein the first SERS active nanoparticle is of uniform composition and the second SERS active nanoparticle has different compositions in a core and shell.

14. The proximity assay of claim 10 wherein the first SERS active nanoparticle comprises a single metal and the second SERS active nanoparticle comprises a mixture or alloy of two metals.

15. The proximity assay of claim 14 wherein the second SERS active nanoparticle comprises a mixture or alloy of Au and Ag.

16. The proximity assay of claim 9 wherein an absorbance maximum of the first SERS active nanoparticle is separated from an absorbance maximum of the second SERS active nanoparticle by between 200 cm$^{-1}$ and 3500 cm$^{-1}$.

* * * * *